(12) United States Patent
Scribner

(10) Patent No.: US 6,393,327 B1
(45) Date of Patent: May 21, 2002

(54) MICROELECTRONIC STIMULATOR ARRAY

(75) Inventor: Dean Scribner, Arlington, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 91 days.

(21) Appl. No.: 09/635,226

(22) Filed: Aug. 9, 2000

(51) Int. Cl.$^7$ .................................... A61N 1/08
(52) U.S. Cl. ............................................ 607/54
(58) Field of Search .................. 600/558, 383; 607/53, 54

(56) References Cited

PUBLICATIONS

Schwarz et al; Single–Chip CMOS Image Sensors For A Retina Implant System; IEEE Trans. on Circuits and Systems, II: Analog and Digital Signal Processing; vol. 46; No. 7; pp. 870–877; Jul. 1999.

Primary Examiner—Scott M. Getzow
(74) Attorney, Agent, or Firm—John J. Karasek; John Gladstone Mills, III

(57) ABSTRACT

The retinal prosthesis test device is comprised of a thin wafer of glass made from nanochannel glass (NGC) with very small channels perpendicular to the plane of the wafer filled with an electrical conductor forming microwires. One surface of the glass is ground to a spherical shape consistent with the radius of curvature of the inside of the retina. The NGC is hybridized to a silicon de-multiplexer and a video image is serially input to a narrow, flexible micro-cable and read into a 2-D array of unit cells in a pixel-by-pixel manner which samples the analog video input and stores the value as a charge on a MOS capacitor. After all unit cells have been loaded with the pixel values for the current frame, a biphasic pulse is sent to each unit cell which modulates the pulse in proportion to the pixel value stored therein. Because the biphasic pulses flow in parallel to each unit cell from a global external connection, the adjacent retinal neurons are all stimulated simultaneously, analogous to image photons stimulating photoreceptors in a normal retina. A permanent retinal implant device uses a NGC array hybridized to a silicon chip, the image is simultaneously generated within each cell through a photon-to-electron conversion using a silicon photodiode. The photons propagate directly through into the backside of the device. Electrical power and any control signals are transmitted through an inductively driven coil or antenna on the chip. The device collects the charge in storage capacitors via the photon-to-electron conversion process, stimulates the neural tissue with biphasic pulses in proportion to the stored charges, and resets the storage capacitors to repeat the process.

4 Claims, 7 Drawing Sheets

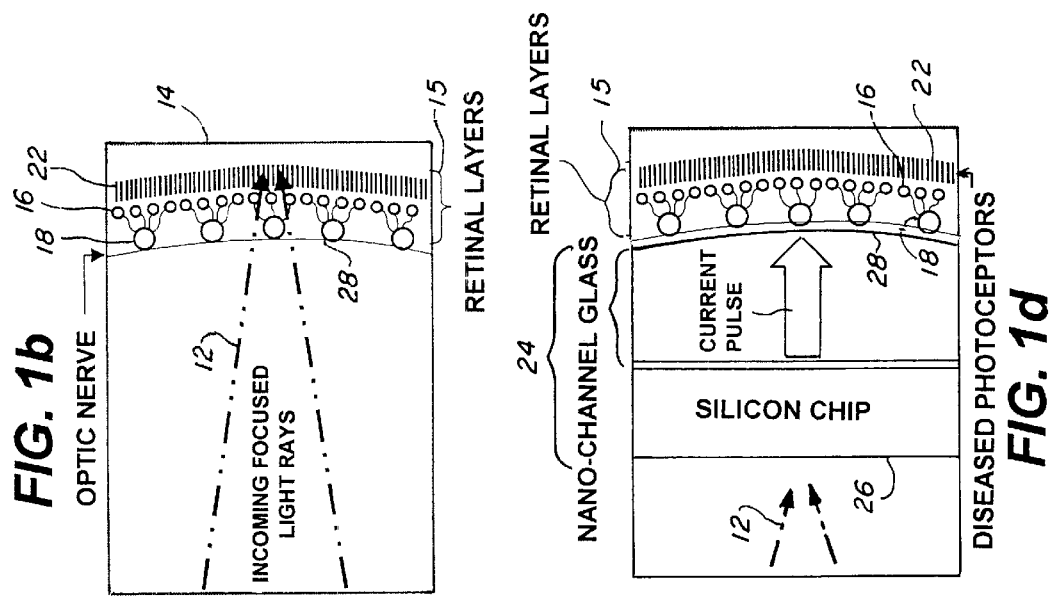
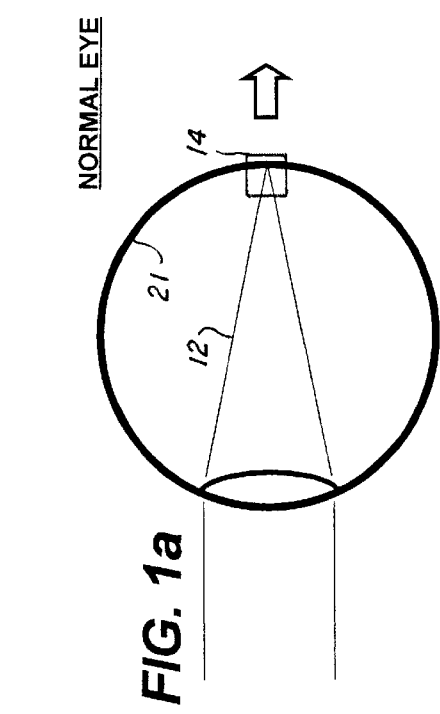
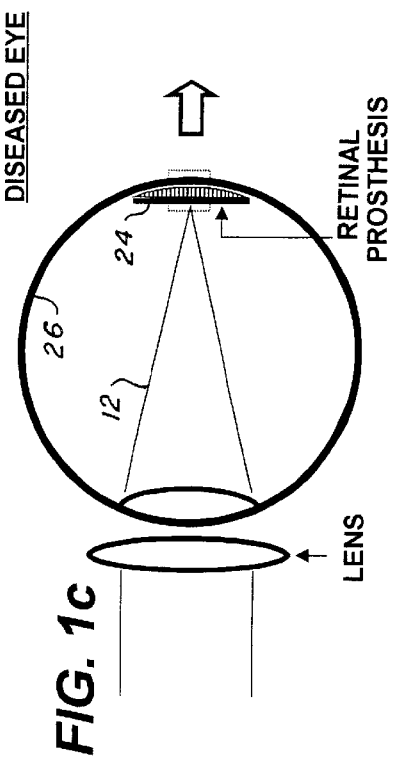

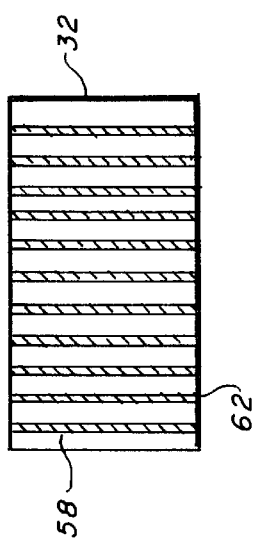
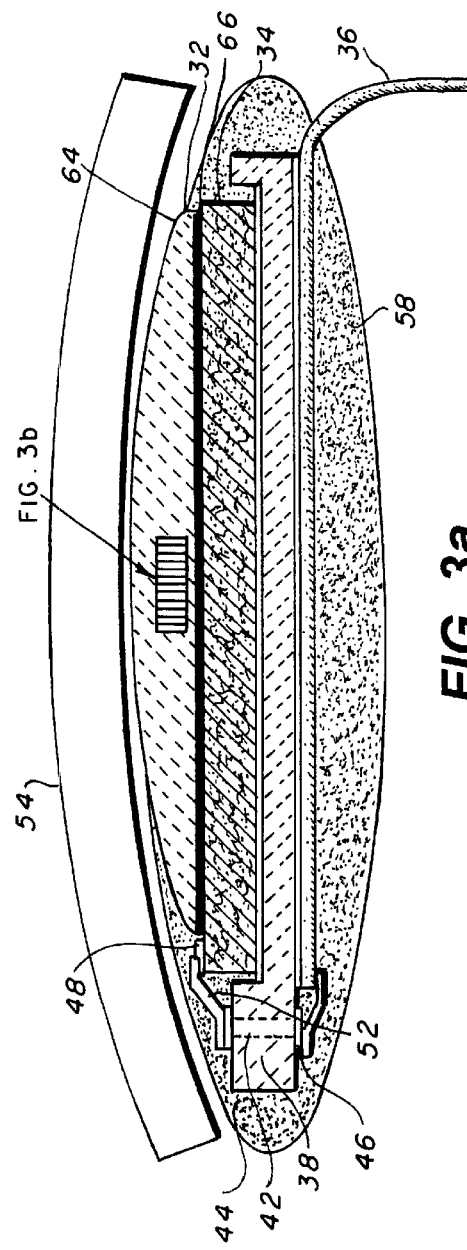

MICROELECTRONIC STIMULATOR ARRAY

BACKGROUND OF THE INVENTION

1. Field of the Invention

This invention deals generally with neural prosthesis, specifically the concept of achieving a retinal prosthesis for blind patients through the creation of an electrical interface between a high-density electrode array and the curved surface of the retina.

2. Description of the Related Prior Art

There is a great deal of recent interest in the area of neural prosthesis, specifically the concept of achieving a retinal prosthesis for blind patients has been hypothesized by a number of researchers and is an active area of medical research. In a normal eye, in a basic concept 10, FIGS. 1a and 1b shows a ray trace of two photons 12 focused on a retina 21. Note that the incoming photons 12 pass through several layers of transparent retinal cells 16 and 18 before being absorbed by the photoreceptors 22. In a damaged eye, a retinal prosthesis device 24, as shown in FIGS. 1c and 1d, is positioned against the retina 21. In this case, the photons 12 are absorbed by a microelectronic stimulating array or device 26 that is hybridized to a glass piece 28 containing an embedded array of microwires. The glass has a curved surface that conforms to the inner radius of the retina 21. The microelectronic imaging device 26 is made of thin silicon containing very large scale integrated (VSLI) circuitry and photon detectors that convert the incident photons 12 to an electronic charge. The charge is then converted to a proportional amount of electronic current which is input to the nearby retinal cell layer 18. The cells fire and a signal is sent to the optic nerve 28.

A typical retinal prosthesis device combines two technologies: first, nanochannel glass (NGC) electrode arrays and secondly a two-dimensional (2-D) multiplexer array. NGC technology employs fiber optic fabrication techniques to produce thin wafers of glass with very small channels perpendicular to the plane of the wafer. Typical NGC wafers that will be required for retinal prosthesis devices are several millimeters in diameter and can contain millions of channels with channel diameters on the order of one micron. The channels are filled with a good electrical conductor and one surface of the glass is ground to a spherical shape consistent with the radius of curvature of the inside of the retina. The electrical conductors on the curved surface should protrude slightly to form efficient electrodes.

The 2-D multiplexer array is similar to infrared focal plane array (IRFPA) multiplexers that are microelectronic devices fabricated at silicon foundries. An IRFPA multiplexer is a 2-D array that reads out the infrared (IR) image captured by a complimentary detector array that converts photons into electrical charge. The charge is integrated and stored in each unit cell for a few milliseconds. The full image is then multiplexed off the array at frame rates compatible with commercial video. For a retinal prosthesis test device that obtains its input image from an external camera, the process is essentially reversed and the device acts as a de-multiplexer. That is, the prosthesis devices will perform de-multiplexing operations, but will be referred to here simply as a multiplexer.

The basic concept is straightforward: visual images can be produced in the brain by electrical stimulation of retinal cells. Two-dimensional arrays of retinal cells, such as ganglion or bipolar cells, can be stimulated using two-dimensional arrays of electrical impulses with the spatial form of an image. The axons of the ganglion cells then transmit the image through the optic nerve and on to the visual cortex. This is in lieu of the normal phototransduction process that occurs in a healthy retina. In approximately 90 percent of blind patients, the photoreceptors are diseased, but the other retinal layers are still responsive to electrical stimulation.

Experimental test procedures, such as shown in FIG. 2, use standard retinal surgical techniques performed in an operating room environment by an ophtalmologist. It is necessary that the patient be administered local anesthesia rather than general anesthesia so that visual perceptions can be orally recorded during the procedure.

There are a number of technical issues to be addressed in designing and fabricating a retinal prosthesis device, particularly if the device is to generate a high resolution image. First, there is the issue of creating an electrical interface between the high-density electrode array and the curved surface of the retina. The electrode array must have a spherical, convexed shape in order to conform to the spherical concaved surface of the retina. The electrode array must be bio-compatible and safe for permanent implantation. Second, the electrical stimulation pulse shapes and repetition rates, while generally well known, may need to be optimized for each individual recipient of a prosthesis device. The pulse amplitude is of course modulated within the retina to be proportional to the pixel value. Third, direct electrical stimulation of the ganglion cells precludes certain image processing functions that normally would have occurred in earlier layers of the retina. Therefore, computationally based image preprocessing operations may need to be performed on the image before stimulation of the retina. Fourth, supplying power to a permanent implant will need to be engineered in a manner such that there are no wires or cables through the eye wall. Fifth, because a normal retina processes image information created by the photoreceptors in a simultaneous manner, it is assumed that a prosthesis device should similarly excite retinal cells in a simultaneous manner, as opposed to sequential raster scan that might cause synchronicity problems downstream in the lateral geniculate nucleus (LGN) or visual cortex.

SUMMARY OF THE INVENTION

An object of this invention is to provide a device for achieving a retinal prosthesis for blind patients.

Another object of this invention is to provide a retinal prosthesis test device for providing visual images to the brain during acute human experiments to achieve electrical stimulation of the retina tissue.

Another object of this invention is to provide a device for implant into the human eye that will allow electrical stimulation of the retinal or any neural tissue so as to provide visual images to the brain.

These and other objects are accomplished by the retinal prosthesis test device and retinal implant device comprising two basic technologies—nanochannel glass (NGC) electrode arrays and infrared focal plane array (IRFPA) multiplexers. In the retinal prosthesis test device, the device is positioned against the retina using standard retinal surgical techniques in an operating room environment. The device is comprised of a thin wafer of glass (NGC) with very small channels perpendicular to the plane of the wafer. The channels are filled with a good electrical conductor forming microwires with one surface of the glass being ground to a spherical shape consistent with the radius of curvature of the inside of the retina. Electrical conductors protrude slightly from the NGC on the curved surface to form electrodes. The NGC is hybridized to a silicon IRFPA multiplexer using indium bump bonds. An image is serially input into the multiplexer via a very narrow, flexible micro-cable. The multiplexer is mounted on a ceramic carrier such that interconnecting bond pads on each are in close proximity to one another. A video image is read into each of the unit cells on the multiplexer in pixel-by-pixel manner. Discrete samples of the analog video are input and stored as electrical charge on a MOS capacitor. After all unit cells have been loaded with the pixel values for the current frame, a biphasic pulse is sent through each unit cell and into the corresponding area of the retina. The biphase pulse is modulated in proportion to the pixel value stored therein. Because the biphasic pulse flows in parallel from a global external connection, the adjacent retinal neurons are all stimulated simultaneously, analogous to image photons stimulating photoreceptors in a normal retina.

A permanent retinal implant device uses an NGC array hybridized to a silicon chip in an identical manner to the retinal prosthesis test device, however, the image is no longer multiplexed onto the chip through a wire from an external camera, but instead, the image is simultaneously generated within each cell through a photon-to-electron conversion using a silicon photodiode. The photons propagate directly into the backside of the device. Electrical power and any control signals are transmitted through an inductively driven coil or antenna on the chip. The device collects the charge in storage capacitors via the photon-to-electron conversion process, stimulates the neural tissue with biphasic pulses in proportion to the stored charges, and resets the storage capacitors to repeat the process.

BRIEF DESCRIPTION OF THE DRAWINGS

FIG. 1a shows a general diagram of a ray trace of photons incident on a retina without a prosthesis device (a normal eye).

FIG. 1b shows an interior view of a ray trace of photons incident on a retina without a prosthesis device (a normal eye).

FIG. 1c shows a general diagram of a ray trace of photons incident on a retina with a prosthesis device (prosthesis device positioned against the retina).

FIG. 1d shows an interior view of a ray trace of photons incident on a retina with a prosthesis device (prosthesis device positioned against the retina).

FIG. 3a shows a side-view of a fully packaged retinal prosthesis test device.

FIG. 3b shows an enlarged view of a nano-channel glass (NCG) electrode array.

DESCRIPTION OF THE PREFERRED EMBODIMENT

Figure 2:
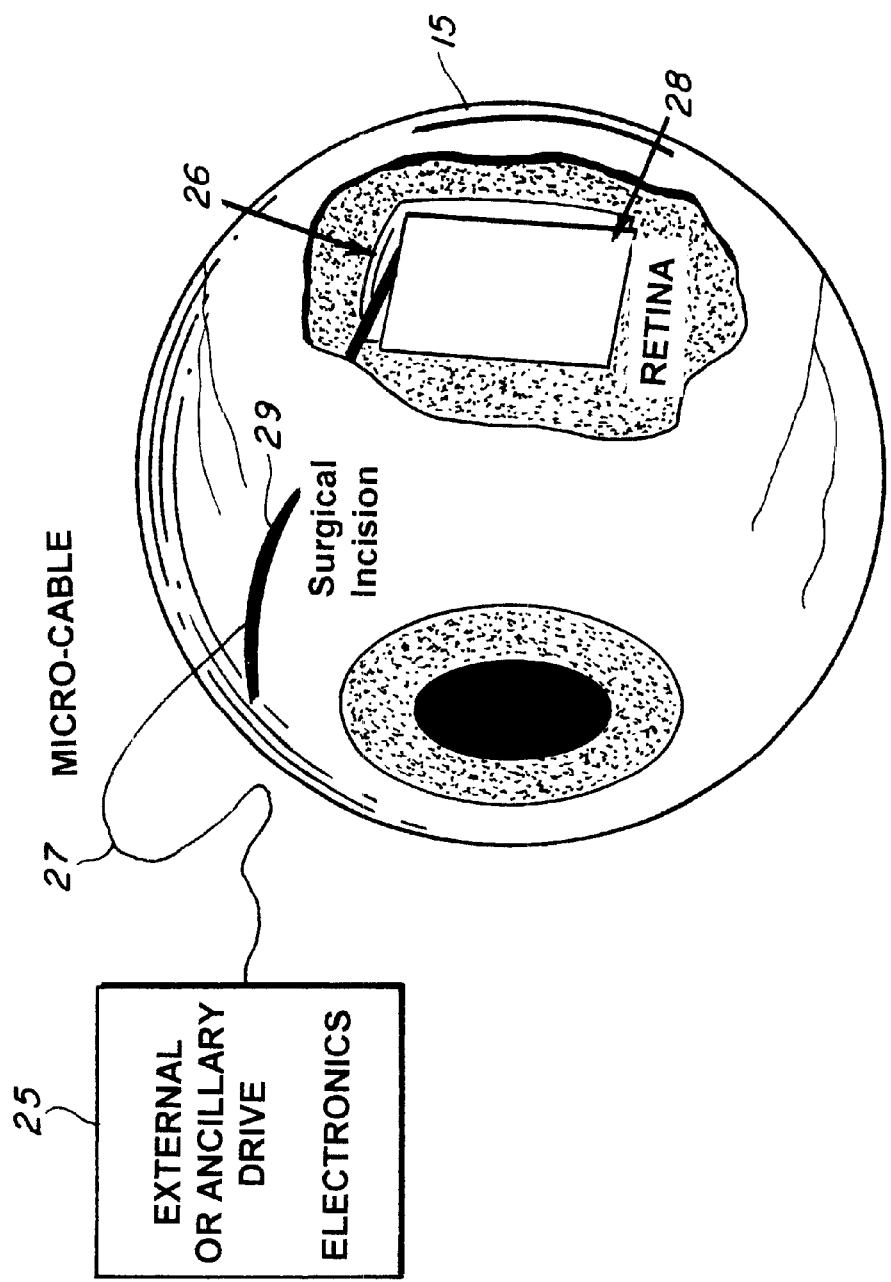
FIG. 2 shows a retinal prosthesis test device positioned against a retina.

In the preferred embodiment of a retinal prosthesis test device utilizing a microelectronic stimulator array 30, as shown in FIG. 3a, the nanochannel glass (NGC) electrode arrays 32 is hybridized to silicon multiplexer 34 using indium bump bonds, a technique from infrared (IR) focal plane array (IRFPA) multiplexers. An image is serially input onto the multiplexer 34 via a very narrow, flexible micro-cable 36. The micro-cable 36 is approximately six inches in length and is custom made using gold leads patterned on polyimide strips. A ceramic carrier 38 with gold-filled via holes 42 provides a mechanically convenient means of routing interconnects from the top-side 44 of the ceramic carrier to the back-side 46. By designing the ceramic carrier such that the top-side contacts to the via-holes 44 are in close proximity to bond pads 48 on the silicon multiplexer 34, the interconnection may be made with conventional tab-bonds 52 (thin gold ribbons fused to interconnects with mechanical pressure as is common practice in the microelectronics industry and is well known to those skilled in the art. This keeps all of the interconnects 52 from protruding above the spherical curved envelop defined by the polished NCG 32 and therefore prevents damage to the tab bond interconnects 52 or to a patients retina 54. A critical issue for any neural prosthesis device is biocompatibility and safety. Because the duration of any tests with the retinal prosthesis test device 30 are very short (less than an hour), biocompatibility issues are primarily reduced to acute effects of the testing and need not address the more difficult chronic issues that arise with permanent implants. Note that the surface of the packaging shown in FIG. 3a consists only of glass 32, platinum (Pt) electrodes 56, and silicon encapsulation 58. However, as with any medical instrumentation, a major safety issue is electrical shock hazard. Note that the purpose of the device is to provide minimal electrical stimulation of retinal tissue using very low voltages and the smallest current possible, i.e., preferably about one volt and 1 $\mu$A per unit cell for about 1 millisecond (every frame at a frame rate of 60 Hz). To protect a patient from any electrical shock, the patient is isolate from high voltages using optocouplers (not shown) which are powered by low voltage electrical batteries (not shown), a technique well known to those skilled in the art.

Specific requirements for the NCG 32 are that the channels 56 making up the NCG 32, as shown in FIG. 3b, be small enough so that many microwires can be connected to each unit cell of the multiplexer array. This is for redundancy and to help simplify the hybridization alignment. If the NCG wires were to approach the size of the unit cell, then a one-to-one alignment and hybridization would be required. This would be very problematic, because of irregularities in the NCG periodicity and the possibility of shorting nearest neighbor cells (not shown). On the other hand, very narrow channels 56 imply very high length-to-width aspect ratios of the channels 56 in the NCG 32. This makes it difficult to fabricate large area NCG 32 samples with the proper thickness. It is expected that a reasonable design size for the channels 56 should be on the order of a micron.

The NCG channels 56 must be filled with a high conductivity material 62, such as platinum, to create microwires. Fabrication of the microwires can be performed using electrodeposition or infusion of molten metal under pressure, techniques that are well known to those skilled in the art. After the channels 56 have been filled with conductive material and the continuity of the microwires has been confirmed, one side of the glass 32 must be polished to create a spherical surface 64. This is accomplished by carefully grinding and polishing of the glass/metal composite. The radius of curvature is nominally half an inch in order to provide a conformal fit against the inside of the retina 54. This is critically important as it allows positioning of the high-density electrodes in the NCG 32 against the retinal 54 tissue. The polishing process will create slightly recessed microwires with respect to the curved NCG 32 surface. This is because the metal is softer than the glass. Therefore further processing may be necessary to create electrodes that protrude slightly above the curved surface 64 of the NCG 32. In preparation for hybridizing the NCG 32 to the multiplexer 34, or the microwires may be hybridized directly to the indium bumps 66 on the multiplexer 34 or the glass is etched so the microwires protrude slightly from the NCG 32. This is similar to the manner used to form the protruding electrodes on the curved side 64 of the NCG 32.

Figure 4:
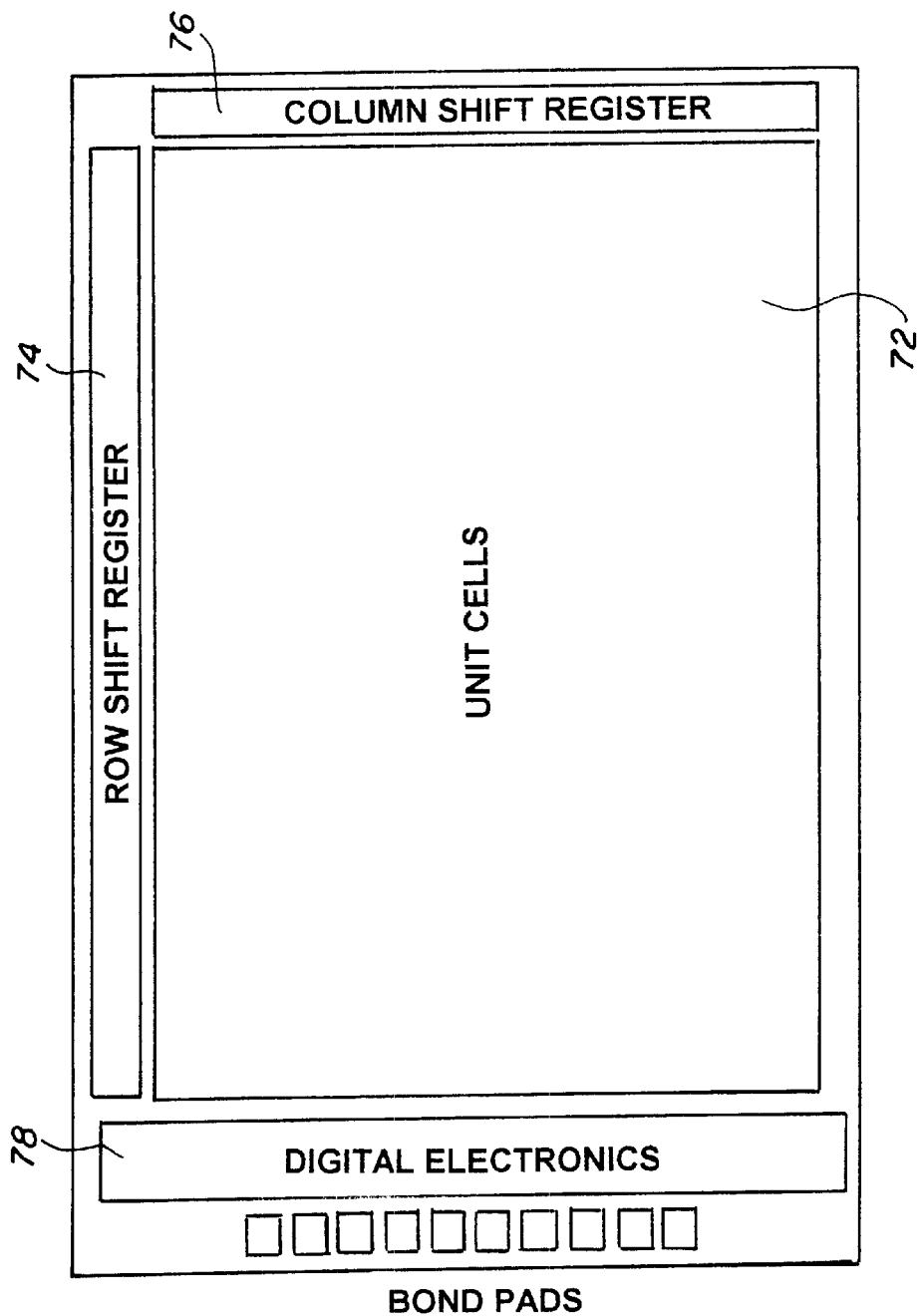
FIG. 4 shows a conceptual layout (floor plan) of a silicon chip for the retinal test prosthesis.

A conceptual layout of the multiplexer 34 is shown in FIG. 4. The silicon multiplexer 34 performs several operations in a sequential order. During the first step, an image is read onto the multiplexer 34, pixel-by-pixel to each unit cell 72. The row shift register 74 and column shift register 76 control the routing into each unit cell 72. The discrete samples of analog video are input and stored as charge on MOS capacitor. This operation occurs every $60^{th}$ of a second in a manner compatible with a RS-170 television format allowing the use of the test prosthesis 30 with standard video equipment. A multiplexer 34 that has a read-on and read-off capability has several input signals including a pixel clock, start-of-frame clock, bias voltage, ground, and analog input (RS-170). A digital electronics block 78 is of major importance because it generates switching pulses that routes image data into the unit cells 72 by controlling the row shift register 74 and the column shift register 76. Without the on-chip digital electronics 78, there might be a dozen or more clocks that would need to be input to the device. That would make the cable 27 from external drive electronics 25 through the eye wall 29 (as shown in FIG. 2) much larger and more cumbersome. The use of IRFPA multiplexer technology greatly simplifies cable 27 problems through the eye wall 29.

Referring again to FIG. 4, after all the unit cells 72 have been loaded with the pixel values for the current frame, the next step is to send a biphasic pulse to that unit cell 72 which in turn is modulated in proportion to the pixel value stored in each unit cell 72. Because the biphasic pulse flows in parallel from a global external connection, the adjacent retinal neurons are all stimulated simultaneously. This is an important feature of the design because it is synchronistic action analogous to imaged photons stimulating photoreceptors in a normal retina. Finally, the electrodes are all connected to ground to prevent any possible charge build up at the electrode-neuron interface.

Figure 5:
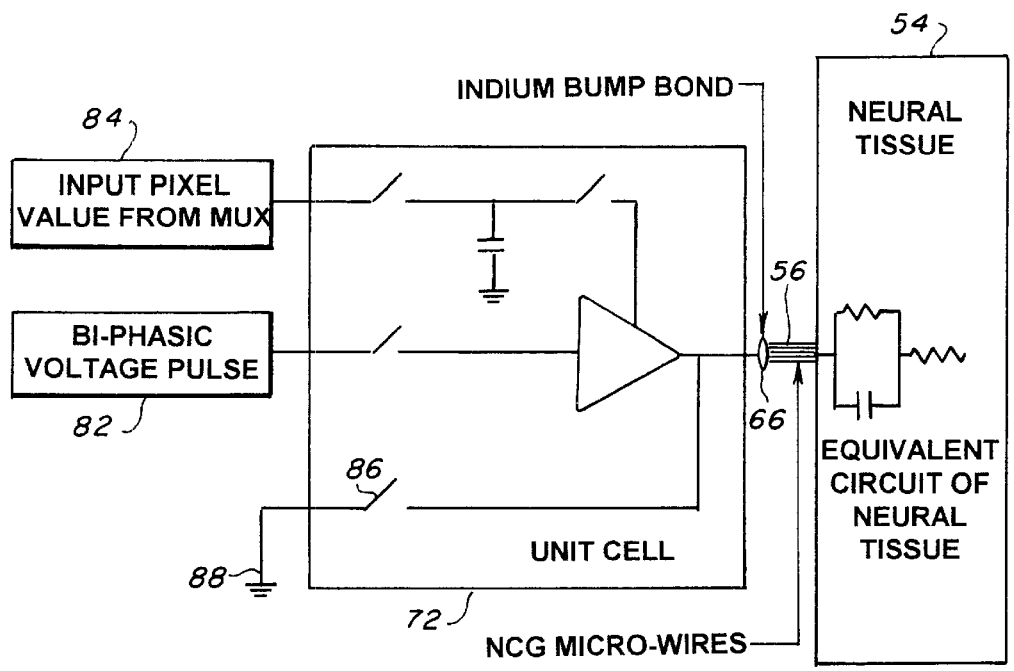
FIG. 5 shows a conceptual design of a unit cell for the retinal prosthesis test device showing the external inputs from off-chip.

There are several important consideration in designing a device that performs all these operations successfully. First the multiplexer 32 operation should be designed with many of the requirements that exist for an IRFPA, for example, good uniformity, low noise, and high dynamic range. Of course, the retinal prosthesis test device 30 moves image data in the opposite direction than an IRFPA multiplexer, that is, image data moves onto the device rather than off the device, but otherwise the specifications are analogous. FIG. 5 shows a generic design for a unit cell 72. Note that the unit cell 72 stores the pixel value and then uses it to modulate the biphasic pulse 82 that is input to the retinal tissue 54 through the NCG 32. Note that the biphasic pulse 82 and the image data 84 are both generated off-chip. This allows for greater flexibility during human testing as any image sequence can be input and combined with any shape of biphasic pulse 82. The switch 86 at the bottom of FIG. 5 provides the capability to connect the retinal tissue 54 to ground 88 to avoid any possibility of charge build-up.

Figure 6:
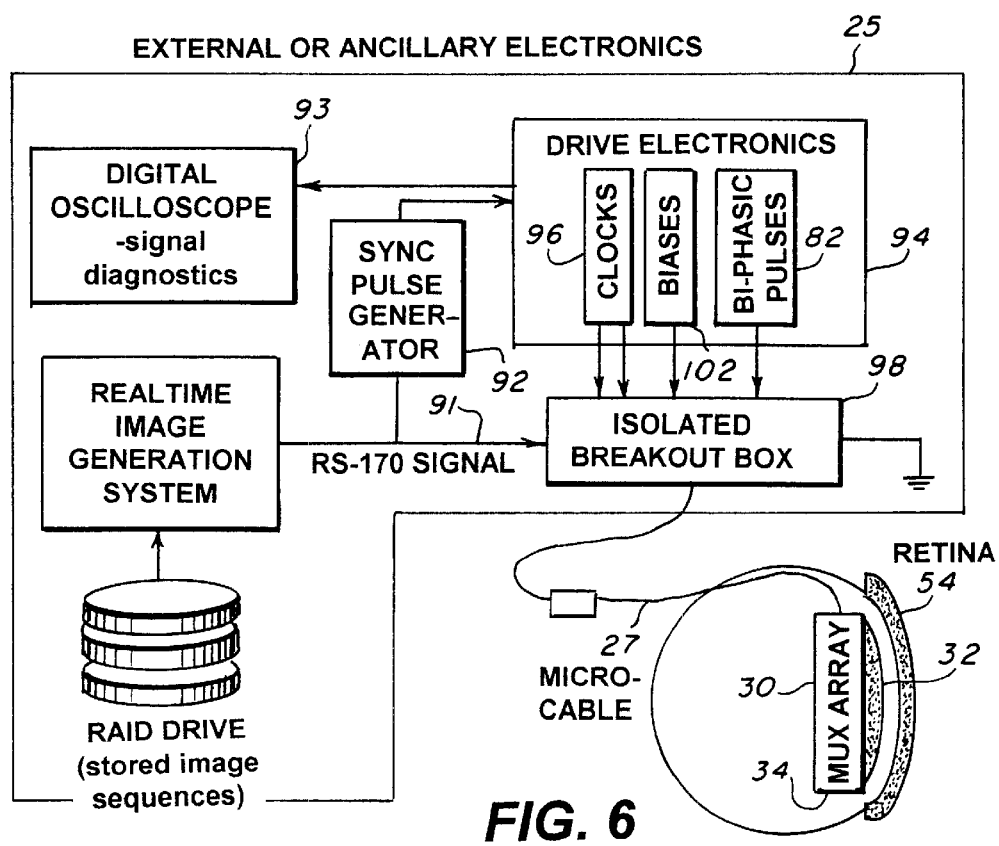
FIG. 6 shows a block diagram of ancillary electronics for the retinal prosthesis test device.

Referring to FIG. 6, the operation of the retinal prosthesis test device 30 during acute experiments is controlled and powered by external ancillary electronics 25. The input signal is an image sequence at data rates fast enough to achieve 60 frames per second. The multiplexer 34 is designed to sample the multiplexed input signal in a manner compatible with the RS-170 format. This allows the retinal prosthesis test device 30 to be interfaced directly with any standard video camera. This includes the use of a computer which stores digital imagery and can display sequential fields at a 60 Hz rate (RS-170 interlaces two fields per frame at a rate of 30 frames per second). The actual control of the microelectronic multiplexer 34 is done with precisely timed pulses generated by a set of signal clocking boards 96 in a manner similar to that used in typical IRFPA's. The sync pulse generator 92 is used to synchronize the RS-170 signal 91 with the clocking pulses 96. Basically, the sync pulse generator 92 detects the beginning of each RS-170 field and then sends a corresponding pulse to the drive electronics 94 that triggers the clocking signals 96 required to control each field of the image data input to the multiplexer 34, synchronizaton of the pulses can be monitored with an oscilloscope 93. The isolated breakout box 98 electrically isolates the human subject from high voltage power supplies. The box 98 contains opto-couplers that isolate the clock 96 and biphasic pulse signals 82 and low voltage batteries supplying bias potentials 102.

The biphasic pulses 82 used to stimulate the retinal tissue 54 may be programmable such that any pulse shapes can be tested. This has several important implications for the development process. First, because the input impedance to the retinal tissue 54 has both a resistive and capacitive reactance associated with it, a square wave voltage pulse will not produce the desired square wave current pulse. Neurobiologists tend to favor square wave current pulses to achieve efficient neural stimulation. With knowledge of the output impedance at the electrode-retina interface, a voltage shape can be computed that will provide a square wave current pulse, thus providing efficient stimulation. Second, there is evidence that various layers of the retina 54 can be stimulated with different shaped pulses—probably because of their differing frequency responses. Specifically, it is expected that either the ganglion or bipolar cells can be selectively stimulated. Stimulating the bipolar cells instead of the ganglion cells has the advantage of reaching more deeply into the retina 54, allowing a more natural form of stimulation.

Direct electrical stimulation of the ganglion cells precludes certain processing functions that normally would have occurred in the earlier layers of the retina 54. Therefore, it may be necessary to perform certain functions on the incoming imagery before stimulation to compensate for the missing processing. Unfortunately, a detailed model of human retinal functions has never been confirmed. Nevertheless, it has been shown that many intracellular recordings from the retinas of rabbits are very similar in mammailian vertebra species in general.

Figure 7:
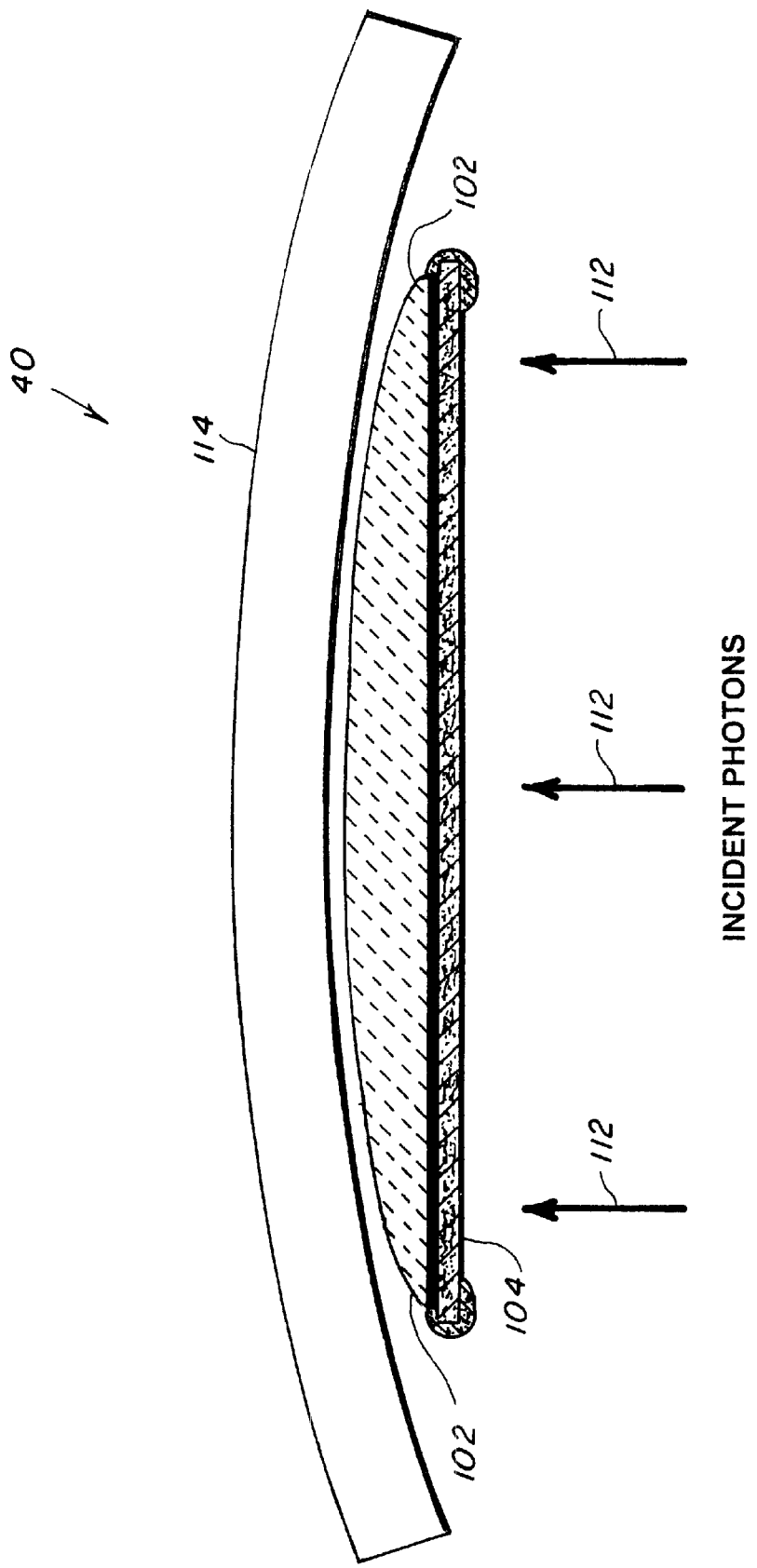
FIG. 7 shows a side-view of a permanent implant device.
Figure 8:
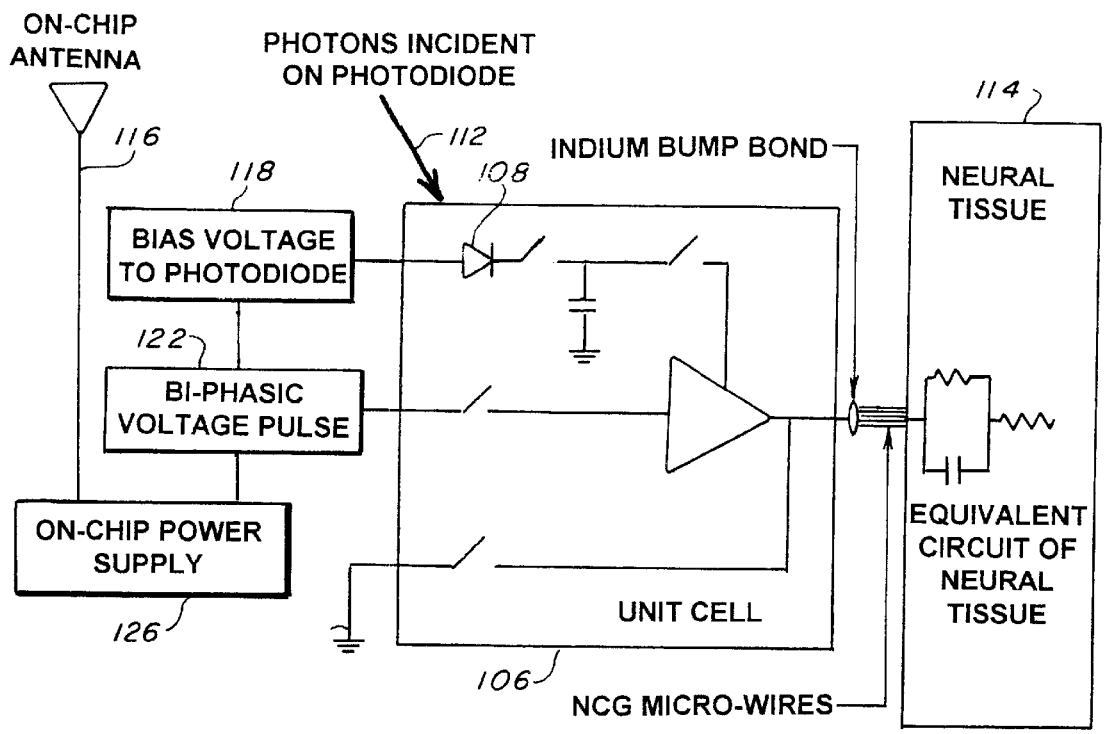
FIG. 8 shows a conceptual design of a unit cell for a permanent implant device.

In another preferred embodiment, a permanent implant device 40, as shown in FIG. 7, that is fully self-contained and responds to incident photons naturally imaged through the lens of the eye, similar to that shown in FIGS. 1c and 1d, is taught. The device 40 is surgically implanted in a patients eye and has with no external connections passing through the eye wall. The basic design of this device 40 is based extensively on the retinal prosthesis test device 30 taught above. Specifically, the permanent implant device 40 would use a NCG array 102 hybridized to a silicon chip 104 in an identical manner to the retinal prosthesis test device 30. However, the unit cell 106 circuitry is redesigned because the image is no longer being multiplexed onto the chip through a cable from an external camera, but instead, the image is simultaneously generated within each unit cell 106 through a photon-to-electron conversion using a silicon photodiode 108, as shown conceptually in FIG. 8. The photons 112 propagate directly into each unit cell 106 because the silicon chip 104 is used in a back-illuminated configuration—essentially the photons 112 enter through the backside of the silicon chip 104.

Packaging the device 40, obviously, differs from that of the retinal prosthesis test device 30. Packaging the permanent implant device 40 requires that the photons 112 be allowed to pass through the backside of the device 40. This is a simple matter of eliminating the ceramic carrier taught in the retina prosthesis test device 30. Thinning the silicon chip 104 is necessary because of the need for good quantum efficiency. The packaging scheme for the permanent implant device 40 is shown in FIG. 7. Note that the silicon chip 104 can be thinned to a few tens of microns so that the overall mass of the object is primarily that of the NCG array 102 making it more amenable for surgical attachment to the retina 114.

Figure 9:
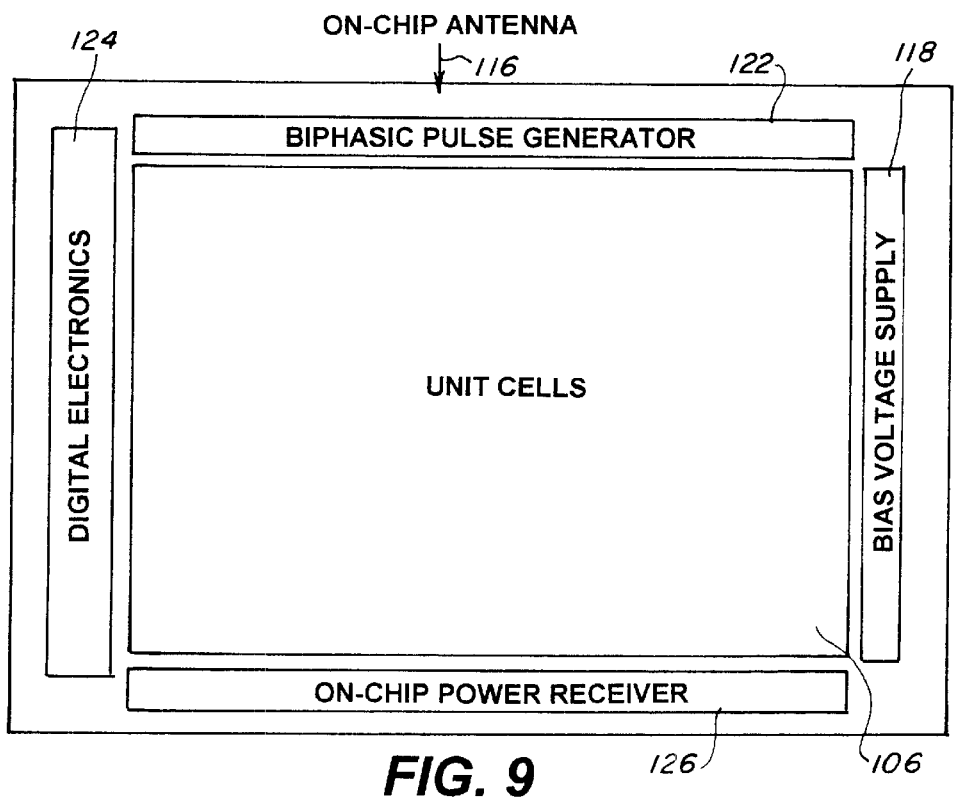
FIG. 9 shows a conceptual layout (floor plan) of a silicon chip for a permanent implant device.

It will be noted that there is no need for any multiplexing functions in the permanent implant device 40, therefore the design of the chip 104 is much simpler. Also there are no ancillary electronics, however, the silicon chip 104 significantly differs from that previously set forth, as shown in FIG. 9. Although there are no multiplexing requirements, there are two new requirements, Specifically, these are external power and command signals necessary to adjust the operation of the device 40. Transmitting power and signals onto the device 40 are implemented with an inductively driven coil or antenna 116. The major on-chip electronic adjustments needed are control of bias supplies 118 and biphasic pulse generator 122 plus the standard digital electronics 124 that supply timing for the simultaneous operation of the unit cell 106 sequences. Again the operation of the device 40 is to collect charge in the storage capacitors of the unit cells. The on-chip power receiver 126 provides conditioned power to operate all the on-chip electronics. The frame rate would be nominally 60 frames per second, but because there is no longer a need to be compatible with the RS-170 format, the frame rate could be adjusted to anything desired.

Packaging of the permanent implant device 40 is very demanding. Along with issues of biocompatibility is the question of device lifetime. Permanent implants might need to operate for several decades. Similar requirements exist for other electronic implants such as cardiac pacemakers and cochlear prosthetics. The encapsulation of the permanent implant device 40 is easier in one respect than that of the retinal prosthesis test device 30 there are no connecting cables to the device 40. In the case of the latter device 30, encapsulation was not a critical issue because the duration of the experiments are typically less than one hour. Cables connected to any neural prosthesis are subject to mechanical forces that over time can damage seals and ultimately cause failures. Because the permanent implant device 40 is completely wireless (no cable connections), simple encapsulation should be achievable with high integrity.

The specific teachings of this approach to neural implants is a new intra ocular device, and has several extremely important advantages over any device taught by the prior art. First, the use of the NCG enables the creation of a curved surface allowing the positioning of the electrodes in extremely close proximity to the retinal cells over a large area. NCG also allows the creation of very small electrodes (on the order of a micron) with very high densities (thousands of electrodes per square millimeter). Regarding the multiplexer for the retinal prosthesis test device 30, as well as the unit cell size for the permanent implant device 40, the unit cell size can be made as small as practical based on the latest microelectronic design rules.

The multiplexer technology taught in the retinal prosthesis test device 30 uses only a small number of electrical leads through the eye wall while allowing a high data rate to the retina. In essence, this allows the input of image sequences to the retina, at high resolution and rapid frame rates. The electrical leads may be fabricated on a small and flexible microcable. This is critical to performing human experiments and testing. This is in comparison to directly coupling all stimulating electrodes to individual leads. For example, a simple 8×8 test array when directly coupled to input electronics outside the eye would require 64 input leads. The cabling and accompanying connectors for such a device becomes very cumbersome.

The devices taught here 30 and 40 basically solves the technical problems of an earlier concept envisioned by the research group at the Wilmer Ophthalmological Institute working with North Carolina State University (NCSU). An approach similar to NCSU is also under study by an MIT/Harvard team. Other efforts are proceeding in the United States, Germany and Japan that build on the basic idea of stimulating retinal cells with a small number of electrodes on a microelectronic chip. However, none of these approaches addresses the difficult issue of high-density electrodes in close proximity to the retina for achieving very high-resolution imagery.

A second approach is to stimulate the retina with a microelectronic chip from behind the retina, either replacing the diseased photoreceptors or positioning the chip just behind them. A third approach is to skip the retina altogether and stimulate the visual center of the brain. In this approach, an array, with penetrating microelectrodes is positioned against a visual cortex. This involves invasive brain surgery through the cranium. From a surgical point of view, the intra ocular approach is the least invasive.

Although this invention has been described in relation to an exemplary embodiment thereof, it will be understood by those skilled in the art that still other variations and modifications can be affected in the preferred embodiment without detracting from the scope and spirit of the invention as described in the claims.

What is claimed:

1. A retinal prosthesis test device comprised of:
   an external image source producing a video image;
   a micro-cable for conducting the video through a patient's eye wall;
   an electronic chip for demultiplexing the video-image into a two-dimensional (2-D) array of unit cells;
   a nanochannel glass electrode array hybridized to said 2-D array of unit cells with indium bumps and electrically connecting each unit cell to adjacent neural tissue; and
   an external electronic circuit board generating a biphasic pulse applied globally to the unit cells through the micro-cable causing an electronic signal to be applied to a human eye wherein it is converted to an electrochemical signal transmitted within the eye to a patient's optic nerve.

2. A device, as in claim 1, wherein the nanochannel glass electronic array is comprised of a hybridized to the microelectronic chip mounted on a ceramic chip carrier, all unit cells controlled by a series of row shift registers and column shift registers for directing the incoming video image to a predetermined unit cell.

3. A permanent retinal implant device comprised of:
- a nanochannel glass electrode array and thinned electronic chip receiving photons through a human iris and converting said photons to a two-dimensional (2-D) spatially discrete electrical signal residing in individual unit cells;
- an electronic unit located externally on a patient for inductively transmitting electrical power and control signals to the electronic chip and nanochannel glass electrode array within the patients eye; and
- a biphasic pulse generated with on-chip electronic circuitry causing an electrical signal to be routed through the nanochannel glass electrode array and applied to adjacent retinal tissue in a human eye where it is converted into an electrochemical signal to be transmitted through retinal neurons within the eye to a patient's optic nerve.

4. A device, as in claim 3, wherein the nanochannel glass electronic array is further comprised of an on-chip antenna for receiving the inductively transmitted signals and applying them selectively to an array of unit cells, digital electronics for controlling the application of the electrical to the retinal tissue, an on-chip power receiver for applying power to the array of unit cells, a bias voltage supply for operating the electronic chip, and a biphasic pulse generator for generating the biphasic pulse, as well as row and column shift registers.

* * * * *